United States Patent
Riddell et al.

(10) Patent No.: US 9,163,258 B2
(45) Date of Patent: Oct. 20, 2015

(54) METHOD FOR THE TREATMENT OF OBESITY

(75) Inventors: Stanley R. Riddell, Sammamish, WA (US); Michael Hudecek, Seattle, WA (US); Christoph Rader, Jupiter, FL (US)

(73) Assignees: Fred Hutchinson Cancer Research Center, Seattle, WA (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/811,712

(22) PCT Filed: Jul. 22, 2011

(86) PCT No.: PCT/US2011/044975
§ 371 (c)(1),
(2), (4) Date: Apr. 4, 2013

(87) PCT Pub. No.: WO2012/012695
PCT Pub. Date: Jan. 26, 2012

(65) Prior Publication Data
US 2013/0202622 A1    Aug. 8, 2013

Related U.S. Application Data

(60) Provisional application No. 61/367,299, filed on Jul. 23, 2010, provisional application No. 61/368,462, filed on Jul. 28, 2010.

(51) Int. Cl.
| | |
|---|---|
| *A61K 35/17* | (2015.01) |
| *A61K 48/00* | (2006.01) |
| *C12N 15/85* | (2006.01) |
| *C07K 16/28* | (2006.01) |
| *C07K 14/71* | (2006.01) |
| *C07K 14/72* | (2006.01) |

(52) U.S. Cl.
CPC ............ *C12N 15/85* (2013.01); *A61K 35/17* (2013.01); *C07K 14/71* (2013.01); *C07K 14/72* (2013.01); *C07K 16/28* (2013.01); *C07K 16/2803* (2013.01); *C07K 2317/622* (2013.01); *C07K 2319/00* (2013.01); *C12N 2740/15043* (2013.01)

(58) Field of Classification Search
CPC ........... A61K 35/17; A61K 2039/5156; C07K 2317/622; C07K 16/28; C07K 14/7051; C07K 14/70521; C07K 16/30; C07K 2319/33; C07K 2319/00; C07K 14/71; C07K 14/72; C07K 16/2803; C12N 15/85; C12N 2501/515; C12N 5/0636

See application file for complete search history.

(56) References Cited

U.S. PATENT DOCUMENTS

| | | | |
|---|---|---|---|
| 2004/0126363 | A1 | 7/2004 | Jensen et al. |
| 2006/0019320 | A1 | 1/2006 | Civenni et al. |
| 2009/0324630 | A1 | 12/2009 | Jensen |
| 2012/0058051 | A1* | 3/2012 | Rader et al. .................... 424/9.1 |
| 2013/0101607 | A1* | 4/2013 | Kipps et al. ................ 424/178.1 |

OTHER PUBLICATIONS

International Search Report for corresponding International Patent Application No. PCT/US2011/044975 mailed Mar. 1, 2012.
Fukuda et al. "Antisera induced by infusions of autologous AD-CD154-leukemia B cells identify ROR1 as an oncofetal antigen and receptor for Wnt5a", PNAS, vol. 105, No. 8, Feb. 26, 2008, pp. 3047-3052.
Baskar et al., "Unique Cell Surface Expression of Receptor Tyrosine Kinase ROR1 in Human B-Cell Chronic Lymphocytic Leukemia," *Clinical Cancer Research* 14:396-404, 2008.
Fukuda et al., "Antisera Induced by Infusions of Autologous Ad-CD154-Leukemia B Cells Identify ROR1 as an Oncofetal Antigen and Receptor for Wnt5a," *PNAS* 105(8):3047-3052, Feb. 2008.
Green et al., "An Established Pre-Adipose Cell Line and its Differentiation in Culture," *Cell* 3:127-133, Oct. 1974.
International Search Report dated Mar. 1, 2012, for International Application No. PCT/US2011/044975, 4 pages.
Jensen et al., "Anti-Transgene Rejection Responses Contribute to Attenuated Persistence of Adoptively Transferred CD20/CD19-Specific Chimeric Antigen Receptor Re-directed T Cells in Humans," *Biol. Blood Marrow Transplant* 16(9):1245-1256, Sep. 2010.
Maher et al., "Human T-Lymphocyte Cytotoxicity and Proliferation Directed by a Single Chimeric TCRξ/CD28 Receptor," *Nature Biotechnology* 20:70-75, Jan. 2002.
Riddell et al., "The Use of Anti-CD3 and Anti-CD28 Monoclonal Antibodies to Clone and Expand Human Antigen-Specific T Cells," *Journal of Immunological Methods* 128:189-201, 1990.
Till et al., "CD20-Specific Adoptive Immunotherpay for Lymphoma Using a Chimeric Antigen Receptor with Both CD28 and 4-1BB Domains: Pilot Clinical Trial Results," *Blood* 119: 3940-3950, Feb. 2012.
Wang et al., "Cellular Immunotherapy for Follicular Lymphoma Using Genetically Modified CD20-Specific CD8+Cytotoxic T Lymphocytes," *Molecular Therapy* 9(4):577-586, Apr. 2004.
Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007.

* cited by examiner

*Primary Examiner* — Daniel C Gamett
(74) *Attorney, Agent, or Firm* — Seed IP Law Group PLLC

(57) ABSTRACT

The present invention relates to therapeutic compositions for treating or preventing obesity and obesity-related disorders in a subject using immunotherapy to target and eliminate adipocytes.

13 Claims, 1 Drawing Sheet

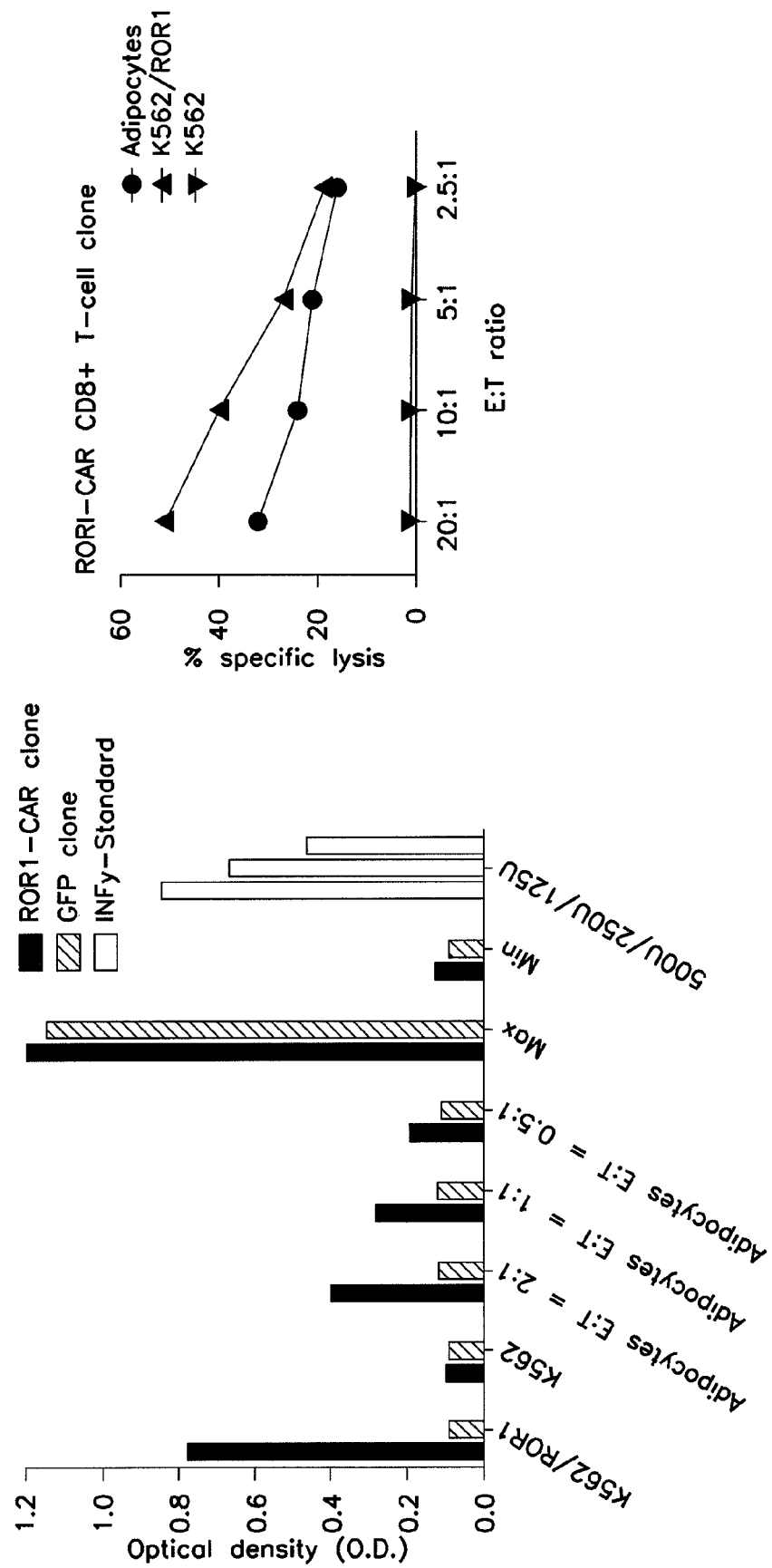

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: ROR1 primer

<400> SEQUENCE: 1
agaggaggaa tgcaccggcc                                                     20

<210> SEQ ID NO 2
<211> LENGTH: 24
<212> TYPE: DNA
<213> ORGANISM: Artificial Sequence
<220> FEATURE:
<223> OTHER INFORMATION: ROR1 primer

<400> SEQUENCE: 2
cacagaaggt acttgttgcg atgt                                                24

<210> SEQ ID NO 3
<211> LENGTH: 20
<212> TYPE: DNA
<213> ORGANISM: Artificial Sequence
<220> FEATURE:
<223> OTHER INFORMATION: ROR1 primer

<400> SEQUENCE: 3
agcgtgcgat tcaaaggatt                                                     20

<210> SEQ ID NO 4
<211> LENGTH: 20
<212> TYPE: DNA
```

-continued

```
<213> ORGANISM: Artificial Sequence
<220> FEATURE:
<223> OTHER INFORMATION: ROR1 primer

<400> SEQUENCE: 4
gactggtgcc gacgatgact                                               20

<210> SEQ ID NO 5
<211> LENGTH: 19
<212> TYPE: DNA
<213> ORGANISM: Artificial Sequence
<220> FEATURE:
<223> OTHER INFORMATION: GAPDH primer

<400> SEQUENCE: 5
gaaggtgaag gtcggagtc                                                19

<210> SEQ ID NO 6
<211> LENGTH: 20
<212> TYPE: DNA
<213> ORGANISM: Artificial Sequence
<220> FEATURE:
<223> OTHER INFORMATION: GAPDH primer

<400> SEQUENCE: 6
gaagatggtg atgggatttc                                               20
```

METHOD FOR THE TREATMENT OF OBESITY

STATEMENT REGARDING FEDERALLY SPONSORED RESEARCH

This application was made with government support under Grant No. CA018029-35 awarded by the National Institutes of Health. The federal government has certain rights in this invention.

This application is a National Stage Application of PCT/US2011/044975, filed 22 Jul. 2011, which claims U.S. Patent Application Ser. No. 61/367,299 filed on 23 Jul. 2010, and U.S. Patent Application Ser. No. 61/368,462 filed on 28 Jul. 2010 and which applications are incorporated herein by reference. To the extent appropriate, a claim of priority is made to each of the above disclosed applications.

BACKGROUND OF THE INVENTION

Obesity is a major public health problem in the United States and western countries and is associated with cardiovascular, endocrine and musculoskeletal disorders in humans. One cause of obesity is the accumulation of lipid material in adipocytes and this accumulation is a major risk factor for cardiovascular disease and diabetes.

Currently, no treatment for obesity exists that directly targets and eliminates adipocytes. Existing treatments for obesity rely on diet to reduce caloric intake and fat accumulation in adipocytes, drugs that reduce appetite, or exercise programs that accelerate metabolic rate. As the failure rate of current treatments is high, it is desirable to identify new ways of treating obesity.

SUMMARY OF THE INVENTION

It is desired to utilize lymphocytes modified to express a target-specific chimeric antigen receptor ("CAR") construct to impart cellular immunotherapy by directly eliminating adipocytes as a novel and innovative approach to treat obesity. An advantage of cellular immunotherapy as disclosed herein is that it specifically targets and eliminates adipocytes permanently. Thus, methods described herein, to treat obesity by eliminating adipocytes with CAR-specific immunotherapy, may have significant commercial utility.

In one aspect, the present invention provides a method of treating obesity which comprises administering a therapeutically effective amount of a lymphocyte modified to express a target-specific chimeric antigen receptor. In one embodiment the administered lymphocyte is a receptor tyrosine kinase-like orphan receptor 1 ("ROR1")-specific chimeric antigen receptor (CAR) transduced CD8+ T cell. In still another embodiment, the cell subset can be CD4+ T cells, NK cells, or any other cell subset suitable for modification to express a target-specific chimeric antigen receptor (CAR). The present disclosure includes compositions of modified lymphocytes useful in the methods described herein.

In a second aspect, the present invention provides a method of eliminating adipocytes in a subject comprising administering a T cell modified to express a target-specific chimeric antigen receptor to the subject. In embodiments, the target specific antigen is a cell surface antigen that is preferentially found on adipocytes.

In another aspect, the present invention provides a method of treating obesity comprising administering a therapeutically effective amount of an endogenous $\alpha\beta$ or $\gamma\delta$ TCR (T cell receptor) T cell or an immunotherapeutic antibody, such as a monoclonal antibody or derivative thereof or combinations thereof.

In another aspect, the present invention provides a method of eliminating adipocytes comprising identifying a subject in need of adipocyte elimination and administering a T cell modified to express a target-specific chimeric antigen receptor.

In another aspect, the invention provides a method of eliminating adipocytes comprising administering a T cell modified to express a target-specific chimeric antigen receptor to a subject and monitoring for adipocyte elimination.

In another aspect, the present invention provides a method of treating obesity comprising identifying a subject suffering from obesity or at risk of obesity and administering target-specific chimeric antigen receptor transduced T cells to the subject.

In another aspect, the present invention provides a method of targeting an adipocyte for elimination comprising providing an adipocyte, determining whether the adipocyte is an adipocyte with a target-specific antigen on its cell surface and identifying the adipocyte for elimination.

In another aspect, the invention provides a kit containing a vessel, tissue sample vial, or composition containing purified target-specific chimeric antigen receptor transduced lymphocyte. In one embodiment the lymphocyte is a CD8+ T cell comprising a receptor tyrosine kinase-like orphan receptor 1 ("ROR1")-specific chimeric antigen receptor.

In some embodiments, the administered lymphocyte comprises a receptor tyrosine kinase-like orphan receptor 1 ("ROR1")-specific chimeric antigen receptor ("CAR") transduced CD8+ T cell, i.e., ROR1-CAR transduced CD8+ T cells or any other cell subset such as, CD4+ T cells, natural killer ("NK") cells, that is suitable for CAR-transduction.

BRIEF DESCRIPTION OF THE FIGURES

FIG. 1(A) shows that ROR1-CAR transduced CD8+ T-cells specifically recognize mature adipocytes.

FIG. 1(B) shows cytolytic activity of ROR1-CAR transduced CD8+ T-cells against mature adipocytes.

DETAILED DESCRIPTION

In one aspect, the present invention provides a method of treating obesity which comprises administering a therapeutically effective amount of a lymphocyte modified to express a target-specific chimeric antigen receptor. In one embodiment the administered lymphocyte is a receptor tyrosine kinase-like orphan receptor 1 ("ROR1")-specific chimeric antigen receptor transduced CD8+ T cell.

In a second aspect, the present invention provides a method of eliminating adipocytes in a subject comprising administering a T cell modified to express a target-specific chimeric antigen receptor to the subject.

In another aspect, the present invention provides a method of treating obesity comprising administering a therapeutically effective amount of an endogenous T cell or an immunotherapeutic antibody, such as a monoclonal antibody or derivatives and fragments thereof.

In another aspect, the present invention provides a method of eliminating adipocytes comprising identifying a subject in need of adipocyte elimination and administering a T cell modified to express a target-specific chimeric antigen receptor.

In another aspect, the invention provides a method of eliminating adipocytes comprising administering a T cell modified to express a target-specific chimeric antigen to a subject and monitoring for adipocyte elimination.

In another aspect, the present invention provides a method of treating obesity comprising identifying a subject suffering from obesity or at risk of obesity and administering target-specific chimeric antigen receptor transduced CD8+ T cells to the subject.

In another aspect, the present invention provides a method of targeting an adipocyte for elimination comprising providing an adipocyte, determining whether the adipocyte is an adipocyte with a target-specific antigen on its cell surface and identifying the adipocyte for elimination.

In another aspect, the invention provides a kit containing a vessel, tissue sample vial, or composition containing purified target-specific chimeric antigen receptor transduced CD8+ T cells.

In one embodiment the CD8+ T cell comprises receptor tyrosine kinase-like orphan receptor 1 ("ROR1")-specific chimeric antigen receptor transduced CD8+ T cells.

In some embodiments, the administered modified T cell comprises a receptor tyrosine kinase-like orphan receptor 1 ("ROR1")-specific chimeric antigen receptor ("CAR") transduced CD8+ T cell, i.e., ROR1-CAR transduced CD8+ T cells.

Modified Lymphocytes

One aspect of the disclosure provides lymphocytes modified to express a target specific antigen receptor. Lymphocytes include both T and B cells. The lymphocytes can be obtained from the subject to be treated or from another source. Lymphocytes can be separated into subpopulations. In embodiments, lymphocytes are separated into naïve, central memory, or effector memory T cells prior to expansion and/or modification. In embodiments, naïve T cells are CD28+ CD62L+ CD95− nd CD45RA+. In embodiments, central memory T cells are CD28+ CD62L+ CD95+ and CD45RA−. In embodiments, effector memory T cells are CD28− CD62L− and CD45RA−.

The invention is described herein primarily with reference to specific T cells modified to express a chimeric antigen receptor ("CAR"), but the invention is not limited to a specific CAR and receptor. CARs comprise a single chain antibody fragment (scFv) that is derived from the variable heavy (VH) and light (VL) chains of a monoclonal antibody (mAb) and linked to the TCR CD3 zeta chain that mediates T-cell activation and cytotoxicity as described in USPTO Publication No. 20040126363 and Maher J, Brentjens R J, Gunset G, Riviere I, Sadelain M. Human T-lymphocyte cytotoxicity and proliferation directed by a single chimeric TCR zeta/CD28 receptor, Nat Biotechnol. 2002; 20:70-75, herein incorporated by reference. Costimulatory signals can also be provided through the CAR by fusing the costimulatory domain of CD28 or 4-1BB to the CD3 zeta chain as described by Maher J, Brentjens R J, Gunset G, Riviere I, Sadelain M. Human T-lymphocyte cytotoxicity and proliferation directed by a single chimeric TCR zeta/CD28 receptor. Nat Biotechnol. 2002; 20:70-75 and Wang J, Jensen M, Lin Y, et al. Optimizing adoptive polyclonal T cell immunotherapy of lymphomas, using a chimeric T cell receptor possessing CD28 and CD137 costimulatory domains. Hum Gene Ther. 2007; 18:712-725, herein incorporated by reference.

CARs are specific for cell surface molecules independent from HLA, thus overcoming the limitations of TCR-recognition including HLA-restriction and low levels of HLA-expression on tumor cells. B-cell lineage differentiation molecules such as CD19 and CD20 are retained on most B-cell tumors, and T cells modified with CD19- and CD20-specific CARs are currently being evaluated in clinical trials. (Jensen M C, Popplewell L, Cooper L J, et al. Anti-Transgene Rejection Responses Contribute to Attenuated Persistence of Adoptively Transferred CD20/CD19-Specific Chimeric Antigen Receptor Re-directed T Cells in Humans. Biol Blood Marrow Transplant. 2010; Epub ahead of print and Till B G, Jensen M C, Wang J, et al.).

In embodiments, a target specific antigen receptor is directed to a target antigen that is preferentially expressed on adipocytes. Such targets are known to those of skill in the art and include AD3 and tyrosine kinase-like orphan receptor 1 ("ROR1"). Methods of introducing a target specific antigen receptor into lymphocytes and selecting cells that express the target specific receptor are known to those of skill in the art.

Isolated lymphocytes or a subpopulation of lymphocytes expressing a target specific antigen receptor can be combined with a physiological acceptable excipient for administration to a subject. Dosages of lymphocytes that are effective for adoptive immunotherapy are known to those of skill in the art and can readily be employed in the treatment of obesity.

Immunotherapeutic Antibodies and Endogenous T Cells

In another aspect, the disclosure provides immunotherapeutic antibodies. Such antibodies are specific for a target antigen that is preferentially expressed on adipocytes. Production and screening of antibodies for specific binding to a target antigen found preferentially on adipocytes are known to those of skill in the art. The preparation of target antigen specific human or humanized antibodies are known to those of skill in the art. Target antigens differentially expressed on adipocytes include, for example, AD3 and tyrosine kinase-like orphan receptor 1 ("ROR1"). Antibodies that specifically bind ROR1 can be prepared and identified using standard methods.

The antibodies that specifically bind to a target expressed on adipocytes can be utilized to prepare a target specific chimeric antigen receptor as described herein. Alternatively, the antibodies, derivatives or fragments thereof can be used in methods of treating obesity or eliminating adipocytes. Antibody derivatives include, for example, antibodies conjugated to cytotoxic molecules or radionuclides, and bispecific antibody constructs. Antibody fragments include, for example, single chain Fv, Fab, Fab', Fab$_2$, Fab$_2$', and the like. Dosages of antibodies useful to treat conditions such as cancer are known to those of skill in the art and can readily be employed to treat obesity.

In embodiments, the disclosure provides target antigen specific T cells isolated from an endogenous T cell repertoire. In an embodiment, the target antigen specific T cells are selected by culturing T cells from a subject in the presence of a target specific antigen or cells bearing the target antigen (e.g. irradiated adipocytes) in a culture medium containing cytokines. Target antigens differentially expressed on adipocytes include, for example, AD3 and tyrosine kinase-like orphan receptor 1 ("ROR1"). The target specific T cells are then cultured in vitro for a period of time sufficient to increase the cell numbers. Target specific T cells can be separated into subpopulations including central memory or effector memory T cells. In embodiments, the separation occurs prior to in vitro expansion. In embodiments, naïve T cells are CD28+ CD62L+ CD95− and CD45RA+. In embodiments, central memory T cells are CD28+ CD62L+ CD95+ and CD45RA−. In embodiments, effector memory T cells are CD28− CD62L− and CD45RA−. In embodiments, the target specific T cells are obtained from the same subject, selected, and expanded and then administered to the subject in order to eliminate adipocytes. In other embodiments, the target specific T cells are obtained from a different source, for example, an unrelated donor, a related donor, or pooled lymphocytes from several donors.

Embodiments, also include a method of treating obesity or eliminating adipocytes in a subject comprising administering an immunotherapeutic antibody that specifically binds a target antigen on adipocytes. A method further comprises also administering target specific T cells to the subject. In embodiments, the target specific T cells, and the immunotherapeutic antibody are specific for the same target antigen. In embodiments, the target antigen is tyrosine kinase-like orphan receptor 1 ("ROR1").

The disclosure also provides use of an immunotherapeutic antibody that specifically binds a target specific antigen, a target specific T cell, or a combination of both for the elimination of adipocytes and/or the treatment of obesity.

Methods and Kits

This invention includes methods for targeting of immature and mature adipocytes with ROR1-CAR transduced CD8+ T cells for elimination as a method of treating obesity and obesity-related disorders. This invention embodies a treatment for obesity using immunotherapy to target a molecule called ROR1 that is expressed on the surface of adipocytes. This invention provides for an immunotherapeutic method of transferring T lymphocytes that target adipocytes for elimination or by transferring antibodies that target and eliminate adipocytes.

The receptor tyrosine kinase-like orphan receptor 1 (ROR1) was originally identified as a highly expressed gene in B-cell chronic lymphocytic leukemia (B-CLL), relative to diffuse large B-cell lymphoma, normal B cells and T cells suggesting that it may serve as a tumor-specific target for therapy of B-cell malignancies. ROR1 has characteristics of an oncofetal gene and is expressed in undifferentiated embryonic stem cells, B-CLL and mantle cell lymphoma (MCL), but not in normal adult tissues apart from adipose tissue and at an early stage of B-cell development. Adipose tissues were the normal adult tissue with the highest level of ROR1 expression. The present invention describes the ROR1 protein as expressed on the cell surface of adipocytes that were generated by differentiation from normal white preadipocytes.

The invention provides for a ROR1-specific chimeric antigen receptor (CAR) with an antigen-binding domain containing the variable heavy and light chain of a ROR1-specific monoclonal antibody, fused to the CD3 zeta chain of the T-cell receptor complex and a CD28 costimulatory domain. When expressed in T cells, the ROR1-CAR conferred specific recognition and killing of ROR1-positive adipocytes providing a novel approach for eliminating adipocytes. Thus, ROR1-CAR specific T-cell therapy is useful for the treatment of obesity.

Embodiments include a method of eliminating adipocytes in a subject, the method comprising administering a lymphocyte modified to express a target-specific chimeric antigen receptor to the subject. In embodiments, the lymphocytes are cytotoxic T cells. In other embodiments, the modified lymphocyte cell is a ROR1-CAR transduced CD4+ T cell or any other cell subset that is suitable for CAR-transduction including naïve, central memory, or effector memory cells. In other embodiments, the method further comprises monitoring tissues for adipocyte elimination.

The disclosure provides methods of identifying target specific antigen for adipocytes. One such method comprises providing an adipocyte, determining whether the adipocyte is an adipocyte with a target antigen on its surface; and if the adipocyte has the target antigen on the cell surface, identifying the adipocyte as a candidate for elimination. In other embodiments a method comprises, obtaining adipose tissue, identifying an adipose specific target antigen, providing a nucleic acid encoding an antigen specific chimeric receptor, wherein the antigen specific chimeric receptor is specific for the target antigen; and modifying a lymphocyte with the nucleic acid. Target specific antigens for adipocytes are known to those of skill in the art and include AD3 or receptor tyrosine kinase-like orphan receptor 1 (ROR1).

The disclosure also provides use of a modified lymphocyte that targets a specific antigen for the elimination of adipocytes and/or the treatment of obesity. In embodiments, the lymphocyte is a ROR1-CAR transduced CD8+ T cell.

Another aspect of the disclosure provides kits for providing a modified lymphocyte suitable for use in the methods described herein. In embodiments, a kit comprises a vessel containing a purified target-specific chimeric antigen receptor transduced CD8+ T cell, an adipose tissue sample vial containing receptor tyrosine kinase-like orphan receptor 1-chimeric antigen receptor transduced CD8+ T cells, or a composition comprising an target specific antigen receptor modified lymphocyte. In other embodiments, a kit further comprises reagents for separation of naïve, central and effector memory lymphocytes, such as antibodies directed to cell surface antigens as described herein. In yet other embodiments, the kit comprises a nucleic acid encoding a target specific chimeric antigen receptor and instructions for separating lymphocytes into a subpopulation and transducing the lymphocytes. In embodiments a kit comprises, an antibody that specifically binds to adipocytes and can be used for imaging or otherwise monitoring a subject for a decrease in the number of adipocytes after treatment with the modified lymphocytes as described herein.

In other embodiments, a kit includes an immunotherapeutic antibody that specifically binds to a target antigen preferentially expressed on adipocytes. In embodiments, the immunotherapeutic antibody is a derivative or fragment thereof. In embodiments, the kit further contains a cell expressing the target specific antigen for use in selecting target antigen specific T cells from an endogenous repertoire. In yet other embodiments, a kit further comprises antibodies for separating central memory from effector memory cells and/or reagents for expanding cells in vitro including one or more cytokines. In embodiments a kit comprises, an antibody that specifically binds to adipocytes and can be used for imaging or otherwise monitoring a subject for a decrease in the number of adipocytes.

EXAMPLES

The present invention is further detailed in the following examples, which are offered by way of illustration and are not intended to limit the invention in any manner. Standard techniques well known in the art or the techniques specifically described below are utilized.

Example 1

Human Subjects

Blood samples were obtained from patients and healthy donors who provided written informed consent to participate in research protocols approved by the Institutional Review Board of the Fred Hutchinson Cancer Research Center (FHCRC). Peripheral blood mononuclear cells (PBMC) and bone marrow mononuclear cells (BMMC) were isolated by centrifugation over Ficoll-Hypaque (Sigma, St. Louis, Mo.), and cryopreserved in RPMI, 20% human serum and 10% dimethyl sulfoxide.

Cell Lines

Epstein-Barr virus transformed B-cells (EBV-LCL) were generated as described in Riddell S R, Greenberg P D. The use of anti-CD3 and anti-CD28 monoclonal antibodies to clone and expand human antigen-specific T cells. J Immunol Methods. 1990; 128:189-201. The tumor lines Jeko-1, Rec-1, BALL-1, RPMI-8226, RCH-ACV, SU-DHL-4, FL18 and SUP-B15 were provided by Drs. Oliver Press and Jerald Radich (FHCRC). All cell lines were maintained in RPMI, 10% fetal calf serum (FCS), 0.8 mM L-glutamine and 1% penicillin-streptomycin (LCL medium). K562, Jurkat and 293T cells were obtained from the American Type Culture Collection (Manassas, Va.) and cultured as directed.

Adipocytes were derived by in vitro differentiation of human white preadipocytes obtained from and differentiated in media provided by Promo Cell (Heidelberg, Germany). Preadipocytes and adipocytes were stained with 0.1 μg/mL Nile red (Invitrogen, Carlsbad, Calif.) for 10 min, washed with PBS and analyzed by fluorescent microscopy.

Transfection of K562 Cells with ROR1

For PCR-amplification of the ROR1-gene, total RNA was obtained from B-CLL cells (RNeasyPlusKit; Qiagen, Valencia, Calif.) and reverse transcribed into cDNA with M-MLV Reverse Transcriptase (Invitrogen). PCR was performed with specific primers (ROR1-F: 5'-XhoI-AGAGGAGGAATG-CACCGGCC-3'(SEQ ID NO:1) and ROR1-R: 5'-XhoI-CA-CAGAAGGTACTTGTTGCGATGT-3') (SEQ ID NO:2) using Herculase-II DNA Polymerase (Stratagene, Santa Clara, Calif.). The PCR-product was cloned into the MIGR-1 retroviral vector[21] and sequence verified. Effectene transfection reagent (Qiagen) was used to transfect Platinum-A cells (Cell Biolabs, San Diego, Calif.) with MIGR-1/ROR1 and produce ROR1-encoding retrovirus. K562 cells were retrovirally transduced by centrifugation at 2500 rpm for 60 min at 32° C., expanded and the ROR1-positive subset sort-purified.

Real-Time Quantitative PCR (qPCR)

First-strand cDNA of B-CLL, normal resting and activated B-cells and EBV-LCL was prepared as described above. First-strand cDNA from normal tissues (Human Tissue panels I/II, Blood Fractions) was obtained from Clontech (Mountain View, Calif.). Expression of ROR1 mRNA was analyzed in duplicate and normalized to GAPDH. Amplifications were performed on an ABI Prism 7900 (Applied Biosystems, Carlsbad, Calif.) in a 50 μl reaction consisting of 25 μl Power SYBR Green PCR Master Mix (Applied Biosystems), 2.5 ng cDNA and 300 nM gene-specific forward and reverse primers: ROR1-F 5'-AGCGTGCGATTCAAAGGATT-3'(SEQ ID NO:3), ROR1-R 5'-GACTGGTGCCGACGATGACT-3' (SEQ ID NO:4), GAPDH-F 5'-GAAGGTGAAGGTCG-GAGTC-3' (SEQ ID NO:5) and GAPDH-R 5'-GAAGATG-GTGATGGGATTTC-3'(SEQ ID NO:6). The cycle threshold (Ct) was determined using SDS software v2.2.2 (Applied Biosystems) and the level of gene expression calculated using the comparative $C_t$ method $[2^{-(\Delta\Delta Ct)}]$.

Immunophenotyping

Cell surface expression of ROR1 was analyzed using specific polyclonal goat-anti-human-ROR1 antibody and goat IgG as isotype control (R&D Systems, Minneapolis, Minn.). In brief, $1\times10^6$ cells were washed, resuspended in 100 μl. PBS/0.5% BSA and stained with 10 μl of 25 μg/mL anti-ROR1 antibody or isotype for 30 min at 4° C. After washing, secondary staining was performed with 0.5 μl of APC-conjugated donkey-anti-goat antibody (R&D Systems) for 30 min at 4° C.

Primary B-CLL, normal B-cells, PBMC and BMMC were stained with one or more of the following conjugated mAbs: CD3, CD5, CD8, CD10, CD19, CD34, CD38, CD45, CD45RO, CD62L, CD86 and matched isotype controls (BD Pharmingen, San Jose, Calif.). Flow analyses were done on a FACSCanto and LSRII, sort-purifications on a FACSAriaII (Becton Dickinson, San Jose, Calif.) and data analyzed using FlowJo software (Treestar, Ashland, Oreg.).

Vector Construction and Generation of Lentivirus

CD20-CAR (CD20-epHIV7) and green fluorescent protein (GFP)-encoding lentiviral vectors (GFP-epHIV7) as described in Wang J, Press O W, Lindgren C G, et al. Cellular immunotherapy for follicular lymphoma using genetically modified CD20-specific CD8+ cytotoxic T lymphocytes. Mol Ther. 2004; 9:577-586.

The ROR1-CAR was encoded in the same vector. A mouse mAb (clone 2A2) that demonstrated specific binding to human ROR1 expressed on primary B-CLL and MCL tumor lines was generated, cloned and characterized.

A codon-optimized nucleotide sequence encoding a scFv containing the VL and VH chain of mAb 2A2 was synthesized (GeneArt, Regensburg, Germany) and cloned into CD20R-epHIV7 using NheI and RsrII restriction sites to replace the CD20-specific scFv. Lentivirus was produced in 293T cells cotransfected with the lentiviral vector and the packaging vectors pCHGP-2, pCMV-Rev2 and pCMV-G using Effectene (Qiagen). Medium was changed 16 h after transfection and lentivirus collected after 48 h.

Lentiviral Transduction and Isolation of CAR-Transduced T-Cell Clones

PBMC from healthy donors and B-CLL patients, and sort-purified CD8+ CD45RO+ CD62L+ central memory T-cells ($T_{CM}$) were activated with anti-CD3 mAb (30 ng/mL) as described in Riddell S R, Greenberg P D. The use of anti-CD3 and anti-CD28 monoclonal antibodies to clone and expand human antigen-specific T cells. J Immunol Methods. 1990; 128:189-201. and exposed to lentiviral supernatant supplemented with 1 μg/mL polybrene (Sigma) and 50 IU/mL recombinant human IL-2 on day 2 and 3 after activation by centrifugation at 2500 rpm for 60 min at 32° C. T-cells were expanded in RPMI, 10% human serum, 2 mM L-glutamine and 1% penicillin-streptomycin (CTL medium) as described in Riddell et al.

After expansion, an aliquot of each transduced T-cell line was stained with biotin-conjugated anti-EGFR (epithelial growth factor receptor) antibody, streptavidin-PE and anti-CD8 mAb. EGFR+ CD8+ T-cells were sort-purified and cloned by limiting dilution (0.5 cells/well), as described in Riddell et al., ROR1-CAR transduced T-cells were identified by staining with biotinylated recombinant Fc-ROR1 extracellular domain fusion protein and streptavidin-PE. Recombinant ROR1-protein was produced in transiently transfected 293F cells (Invitrogen), purified as described in Baskar S, Kwong K Y, Hofer T, et al. Unique cell surface expression of receptor tyrosine kinase ROR1 in human B-cell chronic lymphocytic leukemia. Clin Cancer Res. 2008; 14:396-404, and biotinylated using the BiotinTag kit (Sigma). GFP-transduced CD8+ T-cells were identified by flow cytometry, sort-purified, and cloned in similar fashion.

Chromium Release and Cytokine Secretion Assays

Target cells were labeled with $^{51}Cr$ (PerkinElmer, Fremont, Calif.) overnight, washed and incubated in triplicate at $1$-$2\times10^3$ cells/well with effector T-cells at various effector to target (E:T) ratios. Supernatants were harvested for γ-counting after a 4 h incubation and specific lysis calculated using the standard formula as described in Riddell above. For analyses of cytokine secretion, target and effector cells were plated in triplicate wells at an E:T ratio of 2:1, and INF-γ, TNF-α and IL-2 measured by multiplex cytokine immunoassay (Luminex) in supernatant removed after a 24 h incubation.

Adipocytes from human white preadipocytes by in vitro differentiation were generated as described in Green H, Meuth M. An established pre-adipose cell line and its differentiation in culture. Cell. 1974; 3:127-133 and identified by accumulation of packed intracellular fat droplets that stained positive with Nile red by fluorescent microscopy as described in Greenspan P, Mayer E P, Fowler S D. Nile red: a selective fluorescent stain for intracellular lipid droplets. J Cell Biol. 1985; 100:965-973.

ROR1-CAR transduced CD8+ T cells but not CD8+ T cells transduced with a GFP-expressing control-vector specifically recognize mature adipocytes that had been differentiated in vitro from human white preadipocytes. ROR1-CAR transduced CD8+ T-cells also recognized K562 cells that were stably transfected with the ROR1-gene, but not the native, ROR1-negative tumor cell line K562, confirming the specific recognition of ROR1 on target cells. Effector and target cells were incubated at E:T ratios of 2:1 unless otherwise specified for 24 hours and the production of IFN-γ analyzed by ELISA. The maximum and minimum release of IFN-γ was analyzed by incubating the T-cells with PMA/Ionomycin and medium without target cells respectively. A standard curve was obtained with recombinant human IFN-γ. See FIG. 1(A).

ROR1-CAR transduced CD8+ T-cells but not CD8+ T-cells transduced with a GFP-expressing control-vector specifically lyse mature adipocytes that had been differentiated in vitro from human white preadipocytes. The cytotoxicity was analyzed by chromium release assay at E:T ratios from 20:1 to 2.5:1. Effector and target cells were incubated for 4 hours and the specific cytotoxicity calculated using the standard formula. See FIG. 1(B).

The above specification, examples and data provide a complete description of the method, manufacture and use of the composition of the invention. Since many embodiments of the invention can be made without departing from the spirit and scope of the invention, the invention resides in the claims hereinafter appended. It will be further appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive. It will also be appreciated that in this specification and the appended claims, the singular forms of "a," "an" and "the" include plural reference unless the context clearly dictates otherwise. It will further be appreciated that in this specification and the appended claims, The term "comprising" or "comprises" is intended to be open-ended, including not only the cited elements or steps, but further encompassing any additional elements or steps. The publications and other materials used herein to illuminate the background of the invention, and in particular, cases to provide additional details respecting the practice, are incorporated by reference.

We claim:

1. A method of eliminating adipocytes in a subject, comprising administering a therapeutically effective amount of a composition comprising isolated T lymphocytes modified to express a target specific chimeric antigen receptor, wherein the target is a cell surface antigen preferentially expressed on an adipocyte.

2. The method of claim 1, wherein the isolated T lymphocytes modified to express a target specific chimeric antigen receptor are endogenous T lymphocytes from the subject.

3. The method of claim 1, wherein the target is a receptor tyrosine kinase-like orphan receptor 1 (ROR1) or AD3.

4. The method of claim 1, wherein the T lymphocytes are naïve cells, central memory cells, effector memory cells, or any combination thereof.

5. The method of claim 4, wherein the T lymphocytes are naive cells having a phenotype of CD28+ CD62L+ CD95− and CD45RA+.

6. The method of claim 4, wherein the T lymphocytes are central memory cells having a phenotype of CD28+ CD62L+ CD95+ and CD45RA−.

7. The method of claim 4, wherein the T lymphocytes are effector memory cells having a phenotype of CD28− CD62L− and CD45RA−.

8. The method of claim 4, wherein the T lymphocytes are CD4+, CD8+, or a mixture thereof.

9. The method of claim 8, wherein the T lymphocytes are human.

10. The method of claim 1, wherein the subject is obese or at risk for obesity.

11. The method of claim 1, wherein the subject has an obesity related disorder selected from cardiovascular disease, endocrine disease, musculoskeletal disorder, diabetes, or any combination thereof.

12. The method of claim 1, wherein the subject is a human.

13. The method of claim 1, wherein the T lymphocytes are CD4+, CD8+, or a mixture thereof.

* * * * *